US006893629B2

(12) United States Patent
Prosise et al.

(10) Patent No.: US 6,893,629 B2
(45) Date of Patent: May 17, 2005

(54) DELIVERY SYSTEM FOR A TOOTH WHITENER

(75) Inventors: William E. Prosise, Ramsey, NJ (US);
Timothy G. Bee, Ringwood, NJ (US);
Michael A. Drzewinski, Long Valley, NJ (US)

(73) Assignee: Isp Investments Inc., Wilmington, DE (US)

( * ) Notice: Subject to any disclaimer, the term of this patent is extended or adjusted under 35 U.S.C. 154(b) by 281 days.

(21) Appl. No.: 10/283,439

(22) Filed: Oct. 30, 2002

(65) Prior Publication Data

US 2004/0086468 A1 May 6, 2004

(51) Int. Cl.⁷ .............................. A61K 7/20; A61F 13/00
(52) U.S. Cl. ......................... 424/53; 424/401; 424/435; 424/443
(58) Field of Search ........................... 424/53, 401, 435, 424/443; 427/2.29; 433/80, 89, 136, 138, 141, 146, 215, 217.1, 228.1

(56) References Cited

U.S. PATENT DOCUMENTS

| 5,130,124 | A  | * | 7/1992 | Merianos et al. | .............. | 424/53 |
| 5,800,832 | A  | * | 9/1998 | Tapolsky et al. | ........... | 424/449 |
| 6,582,708 | B1 | * | 6/2003 | Sagel et al. | ................. | 424/401 |
| 6,689,344 | B2 | * | 2/2004 | Chang et al. | ................. | 424/53 |
| 6,780,401 | B2 | * | 8/2004 | Chang et al. | ................. | 424/53 |

* cited by examiner

Primary Examiner—Frederick F. Krass
(74) Attorney, Agent, or Firm—William J. Davis; Walter Katz

(57) ABSTRACT

A delivery system for delivering a tooth whitening substance to a surface of an oral cavity, comprising a film of flexible malleable polymer material having a tooth whitening substance as an integral component of said film, thus providing an active on said oral surface when said film is adhered to the oral surface, said film having a dissolution rate in the aqueous medium of the oral cavity such that the tooth whitening substance can release its active upon said oral surface to act effectively thereon within a predetermined period of time, said film being disintegrable thereafter after effecting its tooth whitening action.

4 Claims, No Drawings

DELIVERY SYSTEM FOR A TOOTH WHITENER

BACKGROUND OF THE INVENTION

1. Field of the Invention

The present invention relates to a system for the delivery of a tooth whitening substance to a portion of a tooth, the entire exposed surface of a tooth, or a number of teeth, and more particularly to such delivery system wherein the substance is protected from erosion within the mouth for a time sufficient to enable an active provided by the substance to cause noticeable tooth whitening. Even more particularly, the present invention relates to disintegration delivery systems, after use.

2. Description of the Prior Art

Dirksing, R. et al, in U.S. Pat. No. 5,989,569 described a delivery system for a tooth whitener using a permanently strip of material on which the tooth whitening substrate was coated in a laminate structure. After tooth whitening, the wearer removed the strip of material from the tooth.

Biss, U.S. Pat. No. 5,077,047 describes a process for the production of $PVP-H_2O_2$ products in the form of free-flowing powders in which a fluidized bed of PVP powders was contacted with finely divided droplets of an aqueous $H_2O_2$ solution.

The following patents illustrate suitable actives in tooth whitening substances: U.S. Pat. Nos. 5,077,047, 5,206,385; 5,108,742; 5,190,749; 5,122,370; 5,183,901; 5,130,124 and 5,312,619.

Accordingly it is an object of this invention to provide a delivery system for a tooth whitening substance which does not require the user to remove any strip after use, and which can be disintegrated or removed easily by aqueous washing after use.

SUMMARY

A delivery system for delivering a tooth whitening substance to a surface of an oral cavity, comprising a film of flexible malleable polymer material having a tooth whitening substance as an integral component of said film, thus providing an active on said oral surface when said film is adhered to the oral surface, said film having a dissolution rate in the aqueous medium of the oral cavity such that the tooth whitening substance can release its active upon said oral surface to act effectively thereon within a predetermined period of time, said film being disintegrable thereafter after effecting its tooth whitening action.

A delivery system wherein said active is $H_2O_2$ complexed with a PVP polymer, said PVP polymer is uncrosslinked or crosslinked PVP, PVP-VA, alkylated PVP or PVP-AA.

A delivery system wherein said oral care substance is present substantially on one side only of said film.

A delivery system wherein said film is made of uncrosslinked or crosslinked $PVP-H_2O_2$ and ethyl cellulose, optionally with hydroxypropyl methyl cellulose and/or glycerol.

DETAILED DESCRIPTION OF THE INVENTION

In accordance with the invention there is provided herein a delivery system for delivering a tooth whitening substance to a surface of an oral cavity, comprising a film of flexible malleable polymer material having a tooth whitening substance as an integral component of said film, thus providing an active on said oral surface when said film is adhered to the oral surface, said film having a dissolution rate in the aqueous medium of the oral cavity such that the tooth whitening substance can release its active upon said oral surface to act effectively thereon within a predetermined period of time, said film being disintegrable thereafter after effecting its tooth whitening action.

A delivery system wherein said active is $H_2O_2$ complexed with a PVP polymer, said PVP polymer is uncrosslinked or crosslinked PVP, PVP-VA, alkylated PVP or PVP-AA.

A delivery system wherein said oral care substance is present substantially on one side only of said film.

A delivery system wherein said film is made of uncrosslinked or crosslinked $PVP-H_2O_2$ and ethyl cellulose, optionally with hydroxypropyl methyl cellulose and/or glycerol.

The invention will now be described in more details by the following examples:

EXAMPLE 1

Tooth Whitening Delivery System 4 g of PVP-hydrogen peroxide complex (20% hydrogen peroxide), made according to U.S. Pat. No. 5,077,047, 3 g of glycerol plasticizer, 4.2 g of hydroxypropyl methylcellulose (Methocel® E4M, Dow Chemical Co.), and 2.8 g of ethylcellulose (Aldrich Chemical) was solubilized in 100 ml absolute ethanol. The solution was then poured onto a film-forming apparatus and the ethanol was gently dried away to produce a malleable film containing about 2–6% hydrogen peroxide. The films were cut into strips and are placed onto wet teeth in the mouth to determine its teeth whitening effect. The films were found to disintegrate on the teeth within about one hour which was sufficient for teeth bleaching to occur upon repeated use.

EXAMPLE 2

Fast Dissolving Tooth Whitening Delivery System 4 g of PVP-hydrogen peroxide complex (20% hydrogen peroxide) made as above, 3 g of glycerol plasticizer, 5.0 g of hydroxypropyl methylcellulose and 2.0 g of ethylcellulose was solubilized in 100 ml absolute ethanol. The solution was then poured onto film-forming apparatus and the ethanol is gently dried away to produce a malleable film containing about 2–6% hydrogen peroxide. The films were cut into strips and placed on wet teeth in the mouth for teeth bleaching effects. The films were found to disintegrate on the teeth within about 20 minutes; teeth bleaching occurred upon repeated use.

EXAMPLE 3

Direct Tooth Whitening Delivery System

A delivery system for a teeth whitener was formulated with less contact of the whitening agent with the buccal cavity while maintaining sufficient contact with the teeth, i.e. less irritating to gums and cheeks.

4 g of crosslinked PVP-hydrogen peroxide complex (20% hydrogen peroxide) made as above and 7 g of ethyl cellulose were mixed into 200 g of absolute ethanol with appropriate plasticizers to obtain the desired film properties. The solution was then poured onto a film-forming apparatus whereupon the cross-linked PVP-peroxide settled to the bottom of the wet film. The ethanol was gently dried away to produce a malleable film containing about 2–7% hydrogen peroxide, which was available on only one side of the film. The other side of the film was essentially water insoluble. The films then were cut into strips and the side with the exposed crosslinked PVP-peroxide complex was placed against the wet teeth in the mouth for teeth bleaching effects. The films generally maintain their integrity within the mouth and release peroxide only on one side, which was sufficient for teeth bleaching to occur, without tissue irritation.

While the invention has been described with particular reference to certain embodiments thereof, it will be understood that changes and modifications may be made which are within the skill of the art. Accordingly, it is intended to be bound only by the following claims, in which:

What is claimed is:

1. A delivery system for delivering a tooth whitening substance to a surface of an oral cavity, comprising a film of a flexible malleable polymer material having a tooth whitening substance dispersed within said film, thus providing an active on said oral surface when said film is adhered to the oral surface, said film having a dissolution rate in the aqueous medium of the oral cavity such that the tooth whitening substance can release its active upon said oral surface to act effectively thereon within a predetermined period of time, wherein said film disintergrates about one hour after being placed in the oral cavity.

2. A delivery system according to claim 1 wherein said active is $H_2O_2$ complexed with a PVP polymer, and said PVP polymer is uncrosslinked or crosslinked PVP, PVP-VA, alkylated PVP or PVP-AA.

3. A delivery system according to claim 1 wherein said film is made of uncrosslinked PVP-$H_2O_2$ optionally with hydroxypropyl methyl cellulose, ethyl cellulose and/or glycerol.

4. A delivery system according to claim 1 wherein the film contains glycerol as plasticizer.

* * * * *